United States Patent [19]

Taylor et al.

[11] Patent Number: 4,869,266

[45] Date of Patent: Sep. 26, 1989

[54] PATIENT MONITORING UNIT FOR SURGICAL USE

[75] Inventors: Terrence H. M. Taylor, Berkeley; Richards P. Lyon, Napa, both of Calif.

[73] Assignee: Stonecrest Systems, Inc., Crystal City, Nev.

[21] Appl. No.: 118,970

[22] Filed: Nov. 12, 1987

Related U.S. Application Data

[63] Continuation of Ser. No. 815,401, Dec. 31, 1985, abandoned, which is a continuation of Ser. No. 666,476, Oct. 30, 1984, abandoned.

[51] Int. Cl.$^4$ .............................................. A61M 1/00
[52] U.S. Cl. ...................................... 128/774; 177/42; 604/66; 604/67
[58] Field of Search .............. 128/630, 714, 774, 782; 177/42–48, 50; 604/35, 50, 65–67; 269/322–325

[56] References Cited

U.S. PATENT DOCUMENTS

| | | | |
|---|---|---|---|
| 3,076,452 | 2/1963 | Rothe | 128/714 |
| 3,497,022 | 2/1970 | Garnett | 177/45 |
| 3,991,424 | 11/1976 | Moran | 128/782 |
| 4,034,361 | 7/1977 | Mortensen | 177/46 |
| 4,363,368 | 12/1982 | Paddon et al. | 177/50 |
| 4,398,429 | 8/1983 | Cook et al. | 128/782 |
| 4,449,538 | 5/1984 | Corbitt et al. | 604/65 |
| 4,492,279 | 1/1985 | Speckhart | 177/45 |
| 4,650,464 | 3/1987 | Ruiz et al. | 604/49 |

FOREIGN PATENT DOCUMENTS

| | | | |
|---|---|---|---|
| 209449 | 6/1960 | Austria | 269/322 |
| 2389112 | 12/1978 | France | 128/774 |
| 2471774 | 6/1981 | France | 269/325 |
| 0132769 | 7/1960 | U.S.S.R. | 128/630 |

OTHER PUBLICATIONS

"High Resolution Scale . . . Bite of Food" by J. Williams; Analogue Dialogue, vol. 10, No. 2, p. 17, 1976.
"Indirect Heart Rate Measuring Device" by Wilbarger et al; Am. J. of Med. Electron., Jul.–Sep. 1964, pp. 194–200.
"Operating Table Controlling Water Balance and Temperature in Cats" by Jorgensen et al; IEEE Trans. on Biomed. Eng., 5/72.
"The Fundamentals of Physics" by Halliday et al; John Wiley & Sons, Inc., N.Y., 1974, pp. 70–74.

Primary Examiner—Lee S. Cohen
Assistant Examiner—David Shay
Attorney, Agent, or Firm—Phillips, Moore, Lempio & Finley

[57] ABSTRACT

A patient monitoring unit is used to follow the actual changes in a patient's weight during the course of a surgical procedure. A patients' fluid inventory is vital to the patients' well being and any significant additions to or losses in body fluids are very significant in the proper management of the patient during surgery. Real time changes in a patient's weight are monitored throughout the surgical procedure. A weighing system utilizing strain gauges or other transducers is built into the operating platform and the output from the transducers is communicated into a computer controller. Angle sensors are provided to measure the tilt at which the operating table may be placed thereby causing an apparent change in weight. The apparent weight change is corrected to the true weight. In the event various portions of the operating table are individually articulated, separate weighing systems and angle sensors are provided for each articulated portion. Weight changes caused by the addition or removal of equipment, supplies, dressings, fluids, etc., to the surgical operating table are factored out, and the system is tared to zero so that only changes in patient weight caused by gain or loss of body fluids are recorded and displayed during the course of the surgery. Any excess gain or loss of body fluids will set off an alarm to alert the surgical team. The pumping rate of an intravenous pump can be adjusted from the computer controller to increase or decrease the rate of infusion of fluids into the patient to compensate for any gain or loss over or below the patient's initial weight.

12 Claims, 4 Drawing Sheets

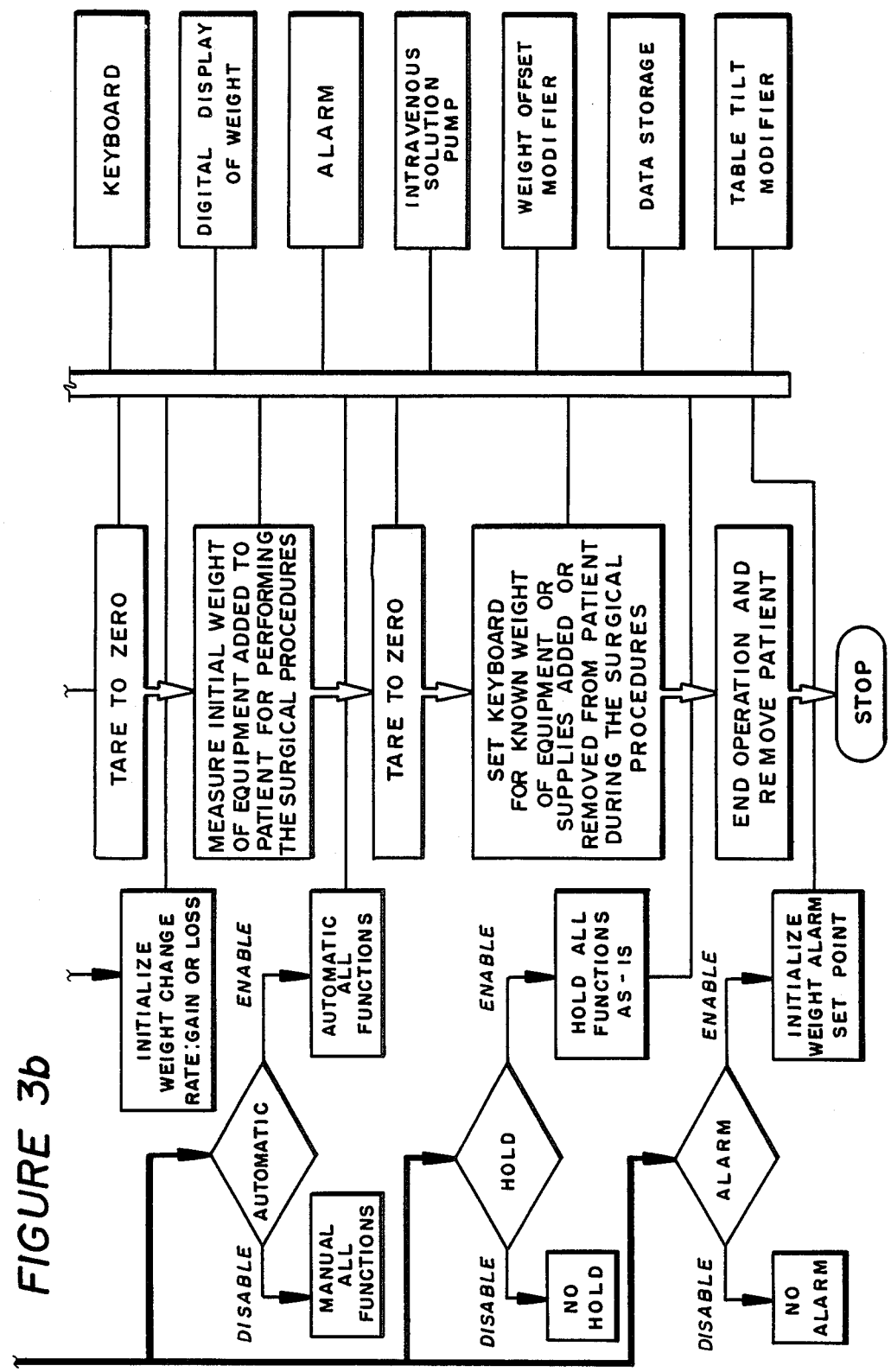

PATIENT MONITORING UNIT FOR SURGICAL USE

This is a continuation of Ser. No. 815,401, filed Dec. 31, 1985, now abandoned; which is a continuation of application Ser. No. 666,476, filed Oct. 30, 1984, now abandoned.

FIELD AND BACKGROUND OF THE INVENTION

Modern surgical procedures have evolved into precisely managed cooperation between the surgeon and the supporting team of anesthesiologist and nurses. Careful observation is maintained over such mechanisms as respiration, blood pressure, pulse rate, EKG and temperature. Any aberration in these signs is noted so that necessary corrective action may be taken, or the surgical procedure modified or aborted, if necessary, to protect the patient's condition.

During surgical procedures fluid and electrolyte losses always occur via lungs and skin, characterized as "insensible loss", and not directly measurable, except by sensitive change in body weight. Sudden losses of fluid can occur in the form of hemorrhage. At present, this type of loss can only be estimated by weighing sponges and pads and by measuring the blood in the suction bottle. Slower losses of fluid and electrolyte, primarily sodium and chloride ions, occur when abdominal and thoracic surgery is in progress as nonvisible secretions by the mucus membranes lining these cavities. During extensive procedures such as with vascular and traumatic problems, fluid and ion losses can be rapid and massive, as much as 1000 cc being lost per hour, and not measurable save by a sensitive weight determination. When signs of circulatory abnormalities appear, the surgeon and anesthesiologist must guess as to the state of the patient's hydration, and treat with intravenous solutions accordingly. Serious overhydration is the commonest result, when, in fact, cardiac and central nervous system abnormalities per se require specific recognition and direct treatment.

A somewhat similar case of fluid overload can occur during a urologic operation, transurethral resection of the prostate gland, or tumors of the bladder, where irrigating fluids containing no electrolytes are used to distend the bladder and prostate for effective vision. These fluids may easily enter the patient's circulation, leading rapidly to overhydration, overload of the circulation and dilution of the electrolytes—all serious problems with short- and long-term consequences. This may happen more frequently when residents are being trained to perform an operation. Continuous sensitive monitoring of the patient's weight and, therefore, water content, would call immediate attention to the hazard at its onset, and an operation would be discontinued safely.

In view of the above, it is apparent that a system for automatically and accurately tracing the patient's loss or gain in weight in real time during surgical procedures would be a valuable adjunct in increasing the safety of such procedures. The present invention is directed to this aspect of surgical management.

BRIEF DESCRIPTION OF THE INVENTION

The present invention is a comprehensive system that includes a device to continually weigh a patient during surgical procedures. Electrical signals generated by the sensitive weight device are continuously fed into a microprocessor and controller means where the data is sent to a data storage means and is also processed to actuate visual weight displays; and as necessary to activate a visual and/or auditory alarm. The system periodically and frequently weighs the patient during the entire surgical procedure and processes the information as outlined above.

The use of a weight device and interpretive system for continuously establishing the minute-to-minute change in the weight of the patient and the rate of change with time of the weight of the patient provides the surgical team with current, historical and predicted data to effect proper management and control of the patient's condition during the surgery.

A suitable device is included to warn the surgical team of any excess loss of gain in weight during the surgical procedures. In addition, a feedback system is provided to automatically adjust the flow rate of any intravenous infusion devices to compensate for fluid loss or gain. This provision is very valuable for patient management during the surgical procedure. Additionally, the system includes a printed record of the patient's weight change during the surgical procedure. This would be valuable in the assessment of any mishaps or unusual events which might occur during the surgery.

Suitable means are also included in the system to account for changes in weight due to surgical equipment added or removed during the course of the operation. Thus, changes in weight not attributable to the patient's own circulatory system and tissue fluids inventory are factored out.

In addition to the aforementioned functions, the system of the invention also includes the aforementioned controller means that controls the infusion of fluids into the patient. More specifically, weight data received from the weight device is utilized by the controller to adjust an infusion pump that provides intravenous solution to the patient. Such means thereby enable the surgery team to automatically control the infusion of intravenous liquids into the patient in response to weight gain or loss during the course of surgery.

The system of the invention is also capable of producing an electronic record and/or printout of the data collected during the course of the operation.

It is therefore an object of the invention to provide a system that continually monitors the weight of a patient during the course of an operating procedure.

It is another object of the invention to provide a system that weighs a patient periodically during an operation procedure and displays the weight for viewing by the operating team.

It is another object of the invention to provide a system that records the changes in a patient's weight during surgical procedures.

It is another object of the system to provide a means to record accurately the weight of any sudden blood loss.

It is still another object of the invention to provide a system that controls the introduction of intravenous fluids into a patient during the course of a surgical procedure.

It is another object of the invention to promptly call attention to any gain in weight of the patient by absorption of the irrigation fluid placed in the patient's bladder during pressure. Such fluid, when taken into the patient's circulatory system, represents a life-threatening situation.

It is yet another object of the invention to provide a system that monitors a patient's weight during surgical procedures and presents a warning if the change exceeds predetermined limits.

It is a further object of the invention to determine by weighing and by electronic computation the rate of change with time of the patient's weight, either loss or gain, and to bring this information to the surgical team's attention by printout of data and/or alarm signal.

An additional object of the invention is to provide a differential patient weight value, either plus or minus, relative to the patient weight at a chosen moment of time when and as the weighing system is "tared" to zero. The patient's weight is stored and printed out upon command, whenever the system is tared to zero.

Other objects and advantages of the invention will become apparent from the following description, drawing figures, and the claims appended hereto.

BRIEF DESCRIPTION OF THE DRAWING

In the drawing:

FIG. 3b is the remaining portion of a schematic block diagram illustrating the procedure of operating the system in the course of a surgical procedure.

DETAILED DESCRIPTION OF THE INVENTION

The invention presents a system to continually monitor in real time a patient's changes in weight during the course of a surgical procedure. The system includes a table wherein the surface upon which the patient is placed includes a support means comprising a plurality of strain gauges that are responsive to the total weight placed thereon. Electrical signals generated by the strain gauges are sent through electrical conductors to a computer wherein the signal from the gauges is averaged out and compared with a calibration curve previously registered within the computer memory to yield a net weight indication. The weight indication is communicated to a display, or displays, where it can be constantly or periodically reviewed by the surgical team. In addition, the weight is constantly compared with a preset upper and lower weight limit level, and with a rate of change weight limit level, and if the value is above or below the preset limits, an alarm is activated to alert the surgical team.

In addition, the rate of change of patient weight with respect to time is continuously computed and compared with preset values. This system includes an evaluation means whereby a sudden increase in weight is automatically interpreted to be the addition of a surgical appliance or other item not representing an increase of body weight by the patient. In this instance the weight increase is automatically deducted from the total weight value otherwise displayed, and the actual net weight of the patient is thus retained and displayed. A similar situation occurs when a sudden decrease in patient weight occurs. In this case, however, the weighing system queries the surgical team to determine if the sudden weight loss is due to removal of an appliance or other material not representative of any loss in the patient's weight budget.

The alternative to the above non-weight loss situation is the removal of a fluid-saturated sponge, for instance. In this case, the weight loss is shown as a true net change in the patient's weight budget.

Addtionally, the weight figure is utilized to regulate and control the operation of a liquid pump to retard, or increase, the weight of fluids infused into the patient in order to bring the weight figure back into the acceptable limits.

A recorder means is also connected to the computer to produce a permanent record of weight fluctuations with time during the surgery period. Included is a means, using the computer memory, to print out in tabular form, upon command, the patient's last weight history prior to instituting each tare command.

The various system components, their relationship to one another, and the operation of the system will be better understood by referring to the accompanying figures.

Figure 1:
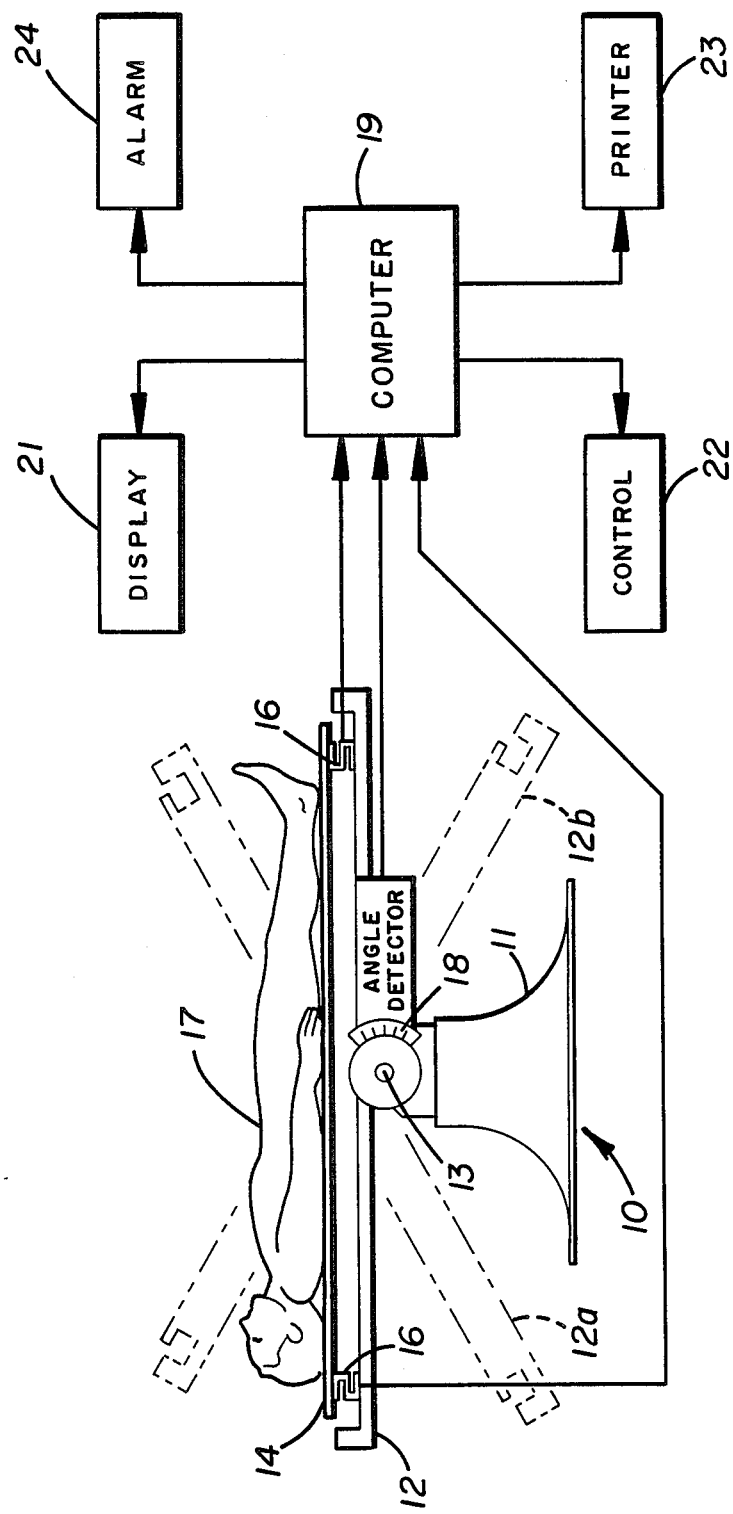
FIG. 1 is schematic illustration of the operating table and the relation of the invention system thereto.

With reference to FIG. 1, an operating table 10 comprises a pedestal 11 upon which is mounted a table frame 12. Frame 12 is affixed to pedestal 11 by means of a pivot 13 that enables the frame to be moved to different angular positions illustrated as 12a and 12b. Frame 12, in turn, supports a patient platform 14 by means of a plurality of strain gauges 16, each of which are affixed both to the frame 12 and, in turn, to the platform 14. It is preferred to provide a strain gauge at each of the four corners of the frame and platform, i.e., 2 gauges at the head and 2 gauges at the foot for the particular table configuration shown.

Platform 14 is adapted to receive a patient 17 upon the upper surface thereof. An angle detector 18 is provided on the operating table base 10 to detect the angle at which the operating platform is positioned. The angle detector may be a cosine potentiometer or similar device which provides an electrical signal proportional to the cosine of the angle at which the operating platform is placed. That is, the apparent weight sensed by the system must be modified by the tilt angle of the table, through the angle measuring device 18 using the well-known cosine law effect of the resolution of forces.

Strain gauges 16 are in electrical communication with a computer 19 that is programmed to process the signals received from the strain gauges and characterize and integrate the same to yield a measure of the total force or weight being exerted thereon by the patient platform, by the patient, by the bedding, and other instrumentation that may be placed in the patient, or on the platform.

That is to say the individual electrical signals received from each of the strain gauges 16 are, of course, characterized, integrated and totalized by the computer 19, no matter where the center of gravity of the patient is positioned on the platform 14.

While the signal emitted by each gauge will, in general, be different from the signal emitted by the other gauges, such differences are integrated after characterizing by the computer programming to yield a total weight regardless of the positioning of the weight or weights on platform 14.

In addition, it will be noted that the relative angle from the horizontal at which platform 14 is positioned will also influence the "apparent weight" recorded by the respective strain gauges. That is, as the tilt of platform 14 is increased from the horizontal in either direction towards the vertical, the apparent weight upon the gauges will decrease. The signal from the angle detector 18 is received by the computer 19 and the apparent weight is corrected to yield the true weight regardless of platform angle.

Thus, a continuous real time measure of the weight upon the gauges 16 is continually processed by computer 19.

Note that the number of strain gauges of other force measuring devices 16 is not limited to four. Likewise the tilt angle is not limited to a single patient platform 14. The present system can be conformed to the regularly available standard surgical operating tables equipped with four independently adjustable angle panels. For compatibility with these four-section tables there will be up to sixteen strain gauges 16 and up to four angle measuring devices 18. While the weight display and control system is identical whether there be a one, two, four or more panel, patient operating table, the integrating system for the strain gauges 16 and the integrating system for the angle measuring devices 18 takes into account the total number of such devices and display the patient's proper weight for processing by the computer 19.

The weight data generated by computer 19 is, in turn, fed into weight display 21, control unit 22, and printer 23. The weight data is also fed into an alarm 14.

Figure 2:
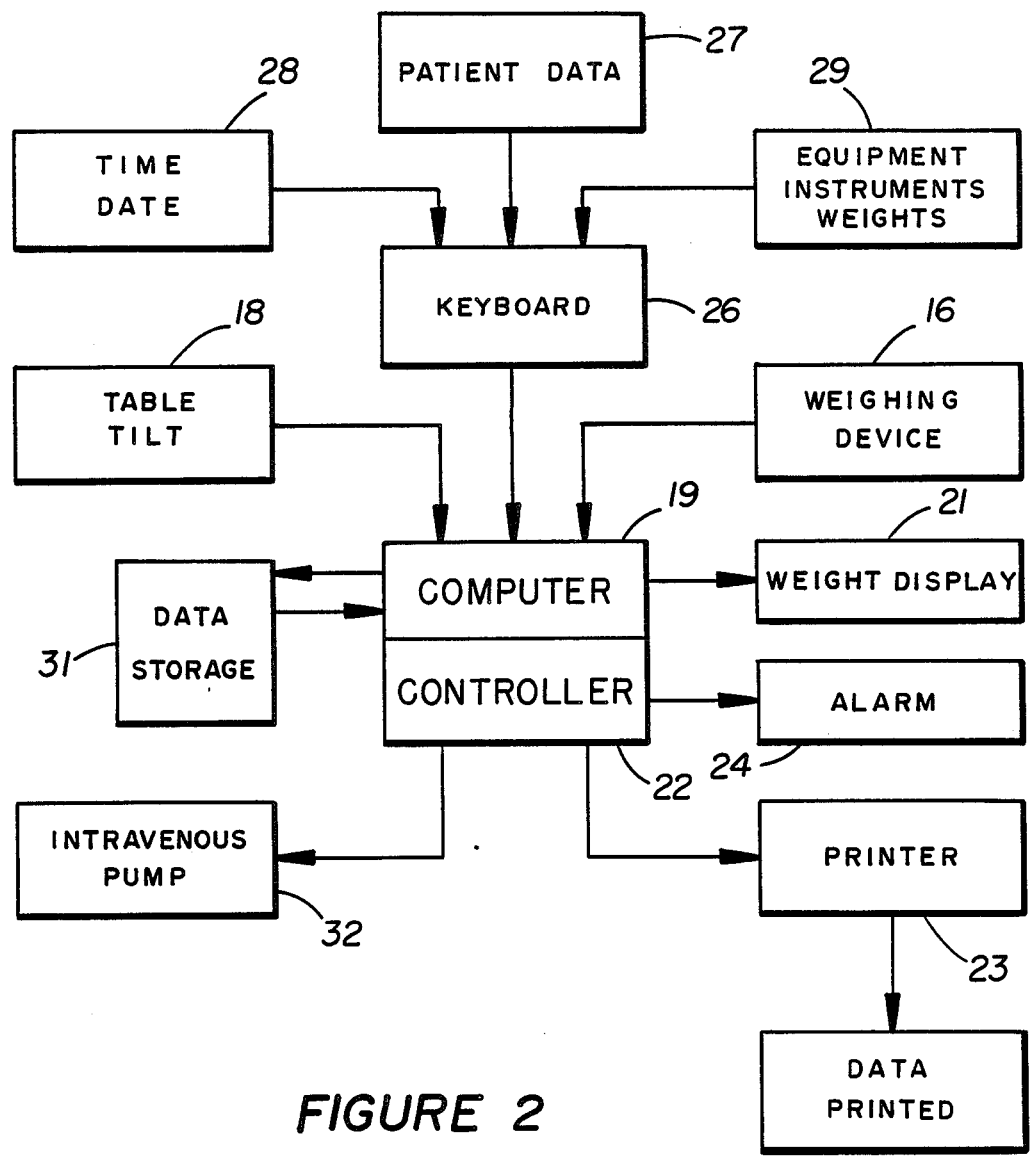
FIG. 2 is a block diagram illustrating the relationship of the various system components.

FIG. 2 presents a block diagram of the interconnection of the various system components in somewhat more detail than the schematic of FIG. 1. In addition to the printout of weight data, the computer system 19 includes an alpha-numeric keyboard 26. This manually operated keyboard 26 allows the surgical team to command the printout of significant and applicable patient data as part of the permanent record for the patient's surgical procedure.

The system also includes the capability of automatically printing out other than weight data from transducers used to monitor the patient's vital signs. All data collectible from the patient can thus be automatically printed out in a real time permanent record showin the actual time that each event occurred. Typically, information such as the time and date 28 of the surgical procedure is manually entered into the computer 19. Similarly, patient data 27 such as name, number, any relevant physical and medical data, can be entered into the computer 19 via keyboard 26.

The weight 29 of various instruments and/or equipment anticipated to be used during the surgical procedure is also manually entered into the computer before the surgical procedure. All of the aforesaid information is retained in the data storage component 31 of the computer 19 where it is available for processing by the computer 19 and controller unit 22.

Computer 19 processes the information received from the keyboard 26, and on a continuing basis from the weighing device 16. Depending upon limits preset into the computer, signals may be sent to the alarm 24 to alert the medical team when the rate of change of weight or the weight itself changes, exceeds, or falls below predetermined limits. Similarly, controller 22 is in electrical communication to an intravenous pump 32. Suitable servo mechanisms are provided with the pump to adjust the flow thereof. Thus, the pump flow rate may be changed in response to excessive weight of fluid losses or excessive fluid gains.

Printer 23 produces a continuous record with time of the weight changes during the course of the operation. The desired patient data is also preserved on the printed record.

Figure 3A:
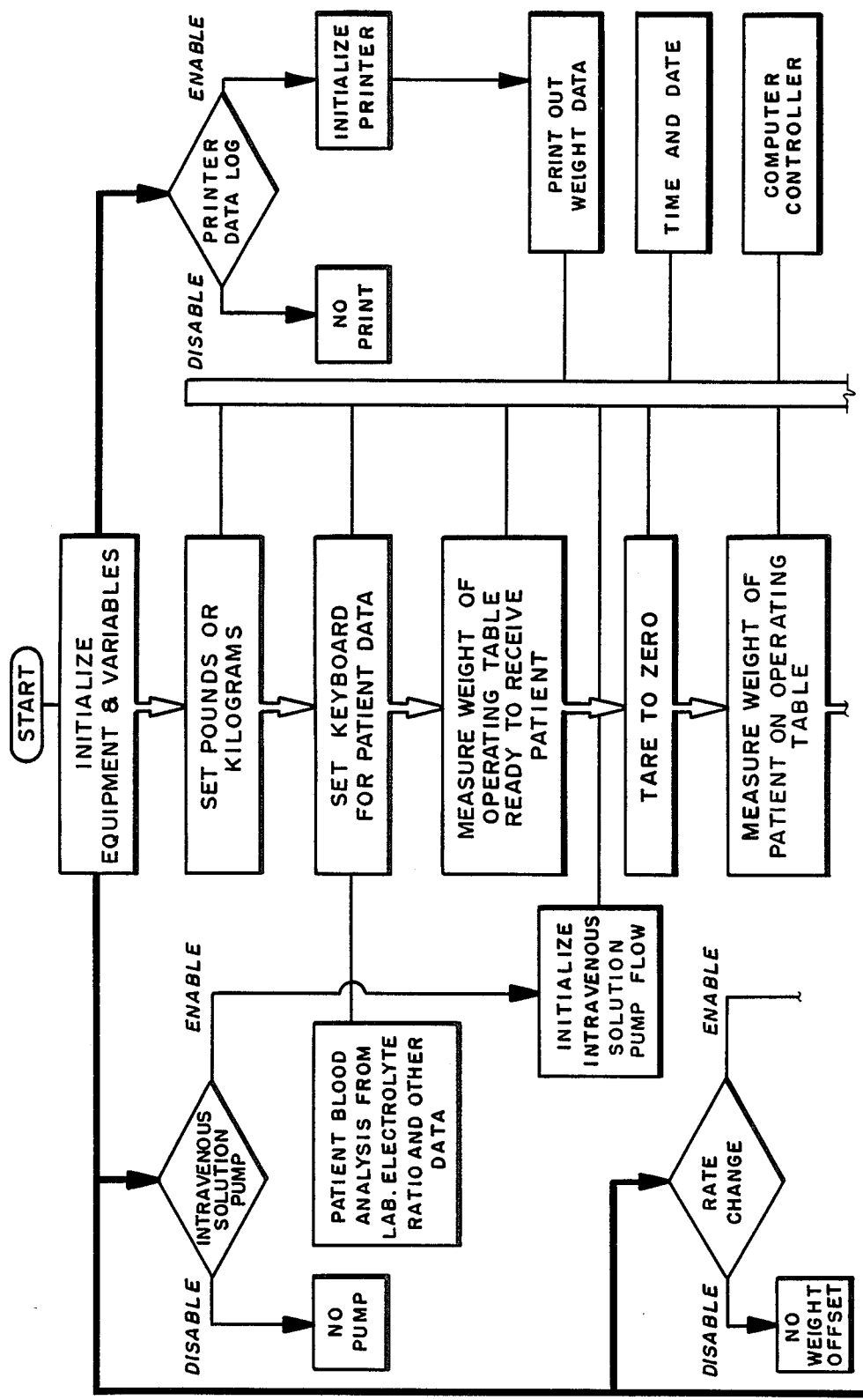
FIG. 3a is a portion of a schematic block diagram illustrating the procedure of operating the system in the course of a surgical procedure.

The operation of the system in the course of a surgical procedure may best be understood with reference of FIGS. 3a and 3b. As can be followed therein, at the START the patient is not on the operating platform. One of the surgical team with responsibility for the monitoring system enters through the keyboard pertinent patient data such as name, number, blood analysis, electrolytic ratios, etc. The computer memory stores key reference control values used repeatedly from operation to operation. Thus, it is not necessary for surgical personnel to repetitiously insert standard information whenever the system is used. The display monitor allows reading out the memory and changing or adding to stored values as desired.

The surgical member also enters into the computer a choice of either the English or metric system for weighing. The display and the printer will thereafter display or print whichever system is chosen.

It normally is desirable to have a record printed out concurrently as the surgical procedure progresses. For this purpose the printe is activated to produce a printout of a log of the data. All data preset into the computer, as well as weight change with time, is then automatically and continuously printed out for reference during or even after the operation procedure, if this is desired. This printout of stored and current information is fully under the control of the monitor member (often the anesthesiologist) of the surgical team. Data can be recalled for reference at any desired time.

At this point, the weight of the operating platform as it stands ready to receive the patient is measured and stored in the computer. By a suitable command the weight of the operating platform has been tared to zero, and patient placed upon the operating platform. When placed upon the platform the patient's weight stresses the weight gauges and a signal is sent to the computer where it is processed to calculate and store the information. The patient's weight is thus displayed and in addition is also sent to the printer.

Since the patient is connected to an intravenous injection system which will control the infusion of fluids during the course of the surgery, the system must be initially set to a desired pump flow rate, with the understanding that the pump flow rate may be modified during the course of the surgical procedure. Initially, however, the rate of flow is set at a nominal level based on the best estimate and the past experience of the surgical team.

Having measured the patient's weight when first placed upon the operating table, the attendant then tares the system to zero once again. Thus, a base is established for the weight and the rate of change of weight of the fluid budget of the patient. Weight changes will trigger the various system functions such as weight display, alarm, etc.

That is to say, when the apparent weight of the system shows a slow increase or slow decrease, e.g., less than 100 grams in 5 minutes or as set by the surgical team, the weight will be stored and displayed (and printed out). If, however, there is a rapid increase, e.g., greater than 100 grams in 5 minutes or as set by the surgical team, then the computer system is set to print out the change with a "fast" code indication thereon. The display, however, will not indicate this "fast" change in weight.

The above rate of weight change conditions are set in order to avoid confusing the surgical team with the inappropriate data or setting off the alarm unnecessarily. Note that the surgical team is alerted when a rapid decrease of weight occurs exceeding, for instance, 100 grams in 5 minutes.

Under this last condition of rapid decrease of weight the weighing system has now way of knowing if a heavy appliance or instrument was removed from the patient, or whether one or more fluid-saturated sponges had been removed from the patient. The removal of an appliance, for example, does not represent a loss of fluid from the patient. By contrast, the removal of a fluid-saturated sponge does represent a loss of fluid. The alarm condition is set "on" until the responsible surgical team member notifies the computer via the keyboard which category, "no loss" or "loss", has occurred. The computer then analyses the patient's weight budget, and the appropriate display, printout, and, if necessary, the alarm condition is automatically set.

If desired, the weight rate change automatic function and/or the alarm may be disabled by the surgical monitor. The data would not then be processed by the computer.

It will be noted that the weight display when the surgery is commenced has been zeroed, thus the weight of the patient, equipment, bedding, etc., has been tared to zero. The changes in weight brought about by equipment addition or removal; dressings addition or removal, will have thus been cancelled out. And, most importantly, the system under the control of the surgical team will only show changes in patient fluid, gain or loss. This will affect the weight display system, however; the display will only be dependent upon any gain or loss in the aforesaid patient fluid weight.

Note that any apparent fluid loss or gain caused by patient bleeding, or by other body fluid budget change, will be recorded directly by the weight measuring system. This is true so long as the fluids are removed from the operating table by removal of saturated dressings, by suction, etc., thus these particular losses will be recorded as a negative value displayed on the weight display panel.

In the event the weight loss exceeds the predetermined but adjustable value set into the system, the alarm will be activated to alert the operating team. Appropriate measures can then be taken to make up for the fluid loss. Under normal circumstances, however, any apparent fluid loss (or gain) will be relayed to the intravenous fluid pump system which may thereby increase (or decrease) its pumping rate and thereby automatically compensate for the weight change and thus retain the patient's weight within the defined limits.

The monitoring of the weight changes, lost or gained, continues during the entire surgical procedure. From a review of FIGS. 3a and 3b it will be noted that the alarm, automatic intravenous pump flow rate change, and the printer function may be placed on "automatic" collectively or individually by the surgical team operator. On the other hand, each function may be selectively disabled to remove these controls from the system.

At the end of the surgical procedure, the patient is removed from the operating platform. The printer will complete printing out the record, and the system will shown the original weight without patient. This provides for a routine system weight check of "before" and "after" conditions.

It will be apparent that employing the system of the invention results in a continual monitoring of the patient's loss or gain of weight during the course of a surgical procedure. The system requires the supervision and input from time to time of at least one member of the surgical team. This member should, to a degree, keep track of equipment, supplies, etc., added or removed from the patient and/or the operating table during the course of the operation. The additions and removals may be entered as necessary or desired into the computer through the keyboard, so that the weighing system readout will truly reflect only patient fluid gains or losses.

Note that while it is desirable for the surgical team to keep track of material added or removed from the operating table, it is not required during the operation of the weighing system in its "automatic" mode. In this instance only, sudden removals of material must be accompanied by the pushbutton command of the surgical team. This pushbutton command informs the weighing system that a particular material removal is either "not a patient weight loss" or "is a patient weight loss". The automatic feature of the weighing system will then cause the correct patient weight budget value to be displayed and recorded.

Thus, the operating team will have available this vital data, providing the information to better manage the patient's fluid budget and general well-being during the course of an operation.

What is claimed is:

1. A patient monitoring unit for use during surgical procedures comprising weighing means incorporated into an operating table for continuously measuring the weight of a patient, computer means having input/output means and processing and storage means, said computer means responsive to said weighing means to enable said computer output means to display changes in the patient's weight as they occur during the course of the surgical procedure, intravenous pump means responsive to said changes in said patient's weight and selectively operable to provide a supply of intravenous fluids to said patient in proportion to said weight change, alarm means connected to said computer means for signaling sudden excessive patient weight changes, said computer means including means for automatically correcting the patient's weight to account for additions to the patient in excess of a predetermined amount during the course of a surgical procedure.

2. The patient monitoring unit of claim 1 wherein said computer means includes means to process weight signals from said weighing means to determine the rate of weight change detected by said weighing means.

3. The patient monitoring unit of claim 1 wherein said computer means enables said computer output the display means to indicate weight changes that are below a predetermined rate of weight change.

4. The patient monitoring unit of claim 1 wherein the input/output means includes printer means for producing printed reports.

5. The patient monitoring unit of claim 1 wherein said computer input means also includes means for manually inputting data into said computer means.

6. The patient monitoring unit of claim 1 also including angle measuring means incorporated in said operating table, and means for communicating the operating table angle of inclination to said computer means.

7. The patient monitoring unit of claim 1 wherein said operating table was several portions thereof being individually articulated for generating a weight signal indicative of the weight of each portion and of any mass placed on said portion, said weighing means including a plurality of individual weighing means incorporated into each articulated portion, means for continuously transmitting weight signals from each said weighing means to the computer means, said computer means including program means for processing weight signals from each of said weighing means to determine the total weight of the patient.

8. The patient monitoring unit of claim 7 further including angle measuring means incorporated into each of the several individually articulated portions of said operating table, and means for communicating the angle of inclination of each portion of the operating table to said computer means.

9. A method for assisting a surgical team during the course of a surgical procedure on a patient, comprising the steps of (a) establishing the patient's weight at the outset of the surgical procedure;

(b) monitoring continually changes in the said patient's weight caused by fluid loss or gain including evaporative loss or gain during the entire surgical procedure;

(c) providing means for displaying said patient's weight so that said changes which may be outside safe limits are brought to the attention of said surgical team;

(d) correcting automatically the patient's weight for additions to the patient in excess of a predetermined amount during the course of the surgical procedure;

(e) providing means to correct the patient's weight for removals from the patient in excess of a predetermined amount during the course of the surgical procedure; and providing selective means for infusing automatically intravenous fluid in response to said monitored changes in said patient weight.

10. The method of claim 9 further including the steps of sounding an alarm when the patient's weight change exceeds or falls below a predetermined upper or lower weight change limit.

11. The method of claim 9 further including the step of detecting changes in the apparent weight of the patient when the patient is tilted from a horizontal plane and the step of correcting the weight change brought about by patient tilting to the true weight of the patient.

12. The method of claim 1 wherein the step of correcting automatically the patient's weight for removals from a patient further includes the steps of accounting for the individual weight of various supplies, equipment and dressings to be used during the surgical procedure and the step of adjusting the monitored weight for each supply, equipment or dressing used during the surgical procedure.

* * * * *

UNITED STATES PATENT AND TRADEMARK OFFICE
CERTIFICATE OF CORRECTION

PATENT NO. : 4,869,266
DATED : Sept. 26, 1989
INVENTOR(S) : Terrence H.M. Taylor and Richards P. Lyon It is certified that error appears in the above-identified patent and that said Letters Patent is hereby corrected as shown below:

IN THE CLAIMS:

Claim 12 should read as follows:

The method of claim 9 wherein the steps of correcting automatically the patient's weight for additions or providing means to correct the patient weight for removals from a patient further includes the steps of accounting for the individual weight of various supplies, equipment and dressings to be used during the surgical procedure and the step of adjusting the monitored weight for each supply, equipment or dressing used during the surgical procedure.

Signed and Sealed this

Eighteenth Day of September, 1990

Attest:

HARRY F. MANBECK, JR.

*Attesting Officer*      *Commissioner of Patents and Trademarks*